United States Patent [19]
Bonnet et al.

[11] Patent Number: 5,674,179
[45] Date of Patent: Oct. 7, 1997

[54] ENDOSCOPE

[75] Inventors: Ludwig Bonnet, Knittlingen, Germany; Steve Morganstern, Atlanta, Ga.

[73] Assignee: Richard Wolff GmbH, Knittlingen, Germany

[21] Appl. No.: 564,901

[22] Filed: Nov. 29, 1995

[30] Foreign Application Priority Data

Mar. 2, 1995 [DE] Germany .................. 295 03 478 U

[51] Int. Cl.$^6$ ...................................... A61B 1/00
[52] U.S. Cl. ..................... 600/105; 600/104; 600/106; 600/138
[58] Field of Search .................... 600/101, 104, 600/105, 106, 108, 135, 138, 153, 156, 164, 171

[56] References Cited

U.S. PATENT DOCUMENTS 2,112,056  3/1938  Wappler .

FOREIGN PATENT DOCUMENTS 77 06 935  8/1977  Germany .

Primary Examiner—Beverly M. Flanagan
Attorney, Agent, or Firm—Cohen, Pontani, Lieberman & Pavane

[57] ABSTRACT

An endoscope for examining the interior of a canal or hollow organ. The endoscope includes an optical system and a channel for an auxiliary instrument such as a laser probe. The distal end of the endoscope shaft and that of the optical system each have a groove-shaped recess so that, upon pulling back of the auxiliary instrument into the endoscope, the probe head, guided by the edge of the recess of the endoscope shaft, is deflected laterally downward of the optical system so as not to impede the field of view of the optical system.

8 Claims, 1 Drawing Sheet

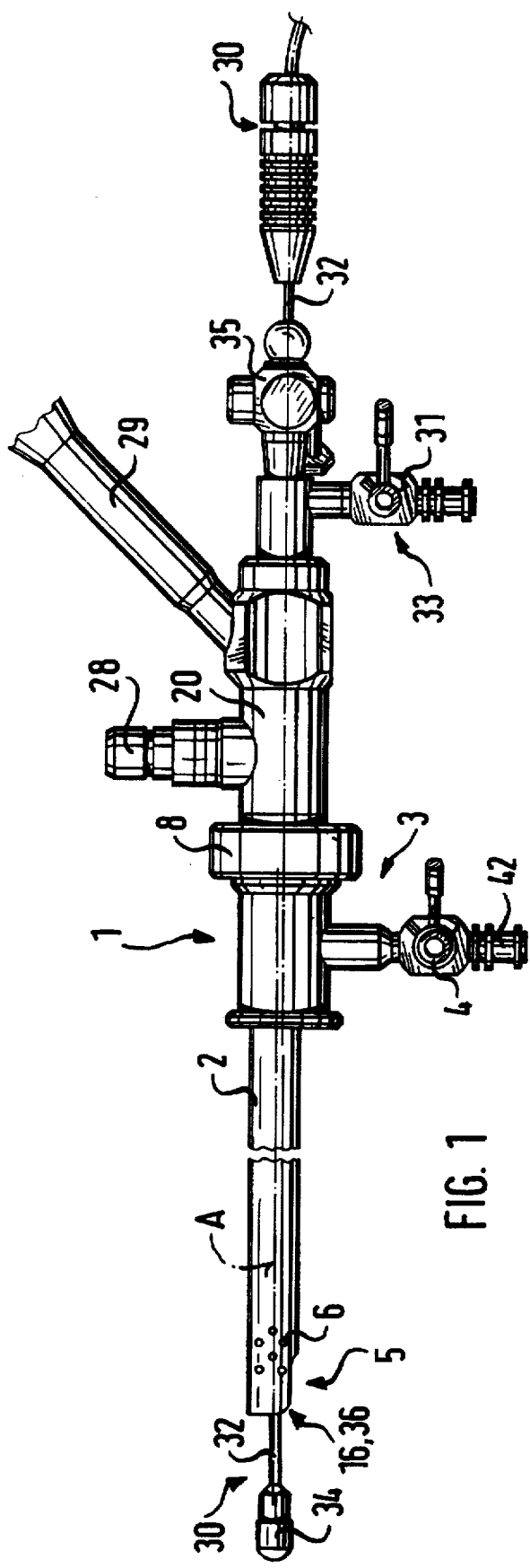
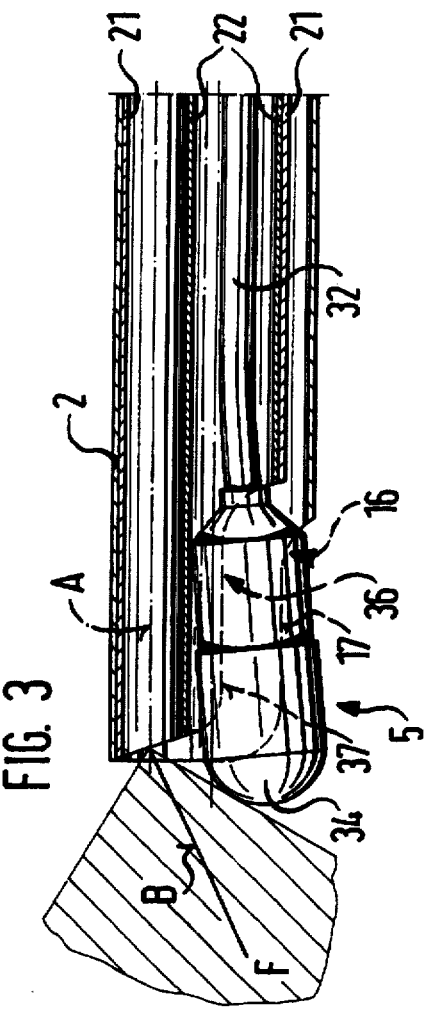
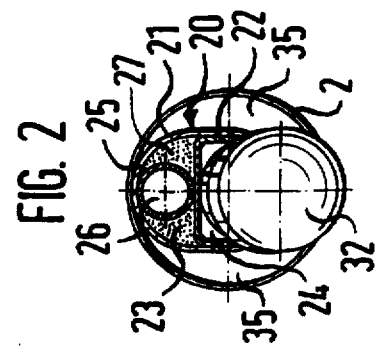
FIG. 1
FIG. 3
FIG. 2

ENDOSCOPE

BACKGROUND OF THE INVENTION

1. Field of the Invention

The present invention relates generally to endoscopes, and more particularly to an endoscope having an optical system and a channel for an auxiliary instrument having a distal head which can be deflected by axial movement of the auxiliary instrument into and out of the field of view of the optical system.

2. Description of the Related Art

An endoscope is known for instance from U.S. Pat. No. 2,112,056. In that endoscope, the head of the axially displaceable auxiliary instrument is deflected from that axis of the endoscope by a ramp which is provided on the endoscope shaft so that, depending on the direction of the axial displacement of the auxiliary instrument, the head lies within the channel or is deflected out of the field of view of the optical system.

Another endoscope with an axially displaceable auxiliary instrument is known from Federal Republic of Germany 77 06 935. In that case, a distal deflection lever is provided which has a mechanism which displaces the deflection lever. By means of the deflection lever, the distal head of the auxiliary instrument is deflected by adjustable angles from the axis of the endoscope. The deflection lever and the required mechanism increase the cost of the endoscope and complicate the handling thereof.

A particular problem results if an endoscope is equipped, for instance, with an axially displaceable laser probe as the auxiliary instrument and the laser probe has a thick distal head which narrows or masks the field of view of the optical system of the endoscope. Thus, for such a case, a solution must be found for bringing the probe head completely out of the field of view of the optical system, while at the same time, avoiding enlargement of the diameter of the endoscope shaft. Due to the diameter of the probe head, such laser probes cannot be introduced, as is customary, from the proximal end through the auxiliary instrument channel of the endoscope, but must be introduced into the endoscope shaft in a so-called "backloading" process. This means that the probe must be first introduced without the head through the channel provided for it and then the probe head is screwed onto the distal end.

OBJECT AND SUMMARY OF THE INVENTION

An object of the present invention, therefore, is to modify an endoscope so that auxiliary instruments, such as for instance, laser probes having large heads, can also be used with it without requiring to enlarge the diameter of the endoscope shaft. Furthermore, a simple solution for the lateral deflection of the probe head is also provided.

The aforementioned object, as well as others which will become apparent to those skilled in the art from the disclosure set forth herein, is achieved by the distal end of the endoscope and that of the optical system each having a groove-shaped recess, such that, upon the pulling back of the auxiliary instrument into the endoscope, guided by the edge of the recess of the endoscope shaft, the probe head is movable at least in part into the free space created as a whole by the recesses and can be brought, with lateral deflection, out of the field of view of the optical system.

The width of the groove-shaped recesses must be greater than the diameter of the shaft of the auxiliary instrument so that the probe head, which has a larger diameter than the probe shaft, can enter at least partially into these recesses upon the pulling back of the probe into the auxiliary channel of the shaft. The edges of the recesses are so shaped that, while the auxiliary instrument is being pulled back, the probe head is deflected laterally of the optical system and thus disappears from the field of view of the optical system.

If the optical axis of the field of view of the optical system forms an angle with the longitudinal axis of the endoscope shaft, then the recesses of the endoscope shaft and of the optical system are arranged so that, with respect to the objective, they are facing radially away from the optical axis of the field of view, i.e., the recesses lie at the lower part of the endoscope shaft and below the optical system when the objective of the optical system lies in the upper part of the endoscope shaft. The axial length of the recesses is approximately equal to or somewhat greater than the length of the head of the auxiliary instrument.

The endoscope of the present invention has a cylindrical outer shaft. The optical system has a substantially oval optical outer shaft and an approximately oval inner shaft. The inner shaft of the optical system has a smaller height than does the outer shaft of the optical system, so that the remaining space of the optical outer shaft can serve to receive the optical system and optical fibers. Furthermore, the free space of the inner shaft serves as a guide channel or an auxiliary instrument channel for the axial guiding of the shaft of the auxiliary instrument; the free space also serves as a flushing channel.

The space remaining between the wall of the cylindrical outer shaft of the endoscope and the outer wall of the oval outer shaft of the optical system can be used as axial suction channels.

The inside spaces of the optical system inner shaft which receives the shaft of the auxiliary instrument or the shaft of the laser probe, preferably has a diameter which is greater than the diameter of the auxiliary instrument shaft or of the laser probe shaft so that an easy sliding of the shaft of the auxiliary instrument or of the laser probe in the channel is assured.

DETAILED DESCRIPTION OF THE DRAWINGS

In the drawings, wherein like reference characters denote similar elements throughout the several views:

FIG. 1 is a diagrammatic showing of an endoscope according to the invention with a laser probe introduced therein, seen in side view;

FIG. 2 is a front view of the distal end of the endoscope shown in FIG. 1; and

FIG. 3 is a diagrammatic longitudinal section through the distal end of the endoscope with the laser probe pulled back.

DETAILED DESCRIPTION OF THE PRESENTLY PREFERRED EMBODIMENT

One embodiment of the endoscope of the invention will be described in further detail below with reference to the drawings. Although this embodiment is based on the use of a laser probe as the auxiliary instrument, the endoscope is not limited to this use. Rather, all types of auxiliary instruments which have a distal head which can be deflected into and out of the field of view of the optical system by axial displacement of the auxiliary instrument along the axis of the endoscope shaft can be advantageously used. As shown in FIGS. 1 and 3, endoscope 1 consists essentially of an outer shaft 2 which has proximally a connection part 3 on which a closable connection 4 for connection to a source of suction (not shown) and a coupling 42 are provided. On the distal end, the outer shaft 2 passes into an end section 5 which, in a lower region, has a recess 16 and lateral suction openings 6. By a coupling 8, an optical system 20 can be coupled to the outer shaft 2.

As is particularly clear from the front view of the distal end of the endoscope shown in FIG. 2, the endoscope optical system 20 has an optical outer shaft 21 and an optical inner shaft 22 located within the optical outer shaft 21. Both optical shafts 21, 22 have, in principle, an oval cross section, the optical inner shaft 22, however, having only about half the height of the largest diameter of the optical outer shaft 21. In this way, the optical system is divided into two spaces 23 and 24. The space 23 contains an optical system objective 26 arranged in a shaft 25. The remaining space 23 is filled with optical fibers 27. The optical fibers 27 end proximally in an optical fiber connection 28. The optical system 20 terminates somewhat further proximally of the optical fiber connection 28 in an eyepiece 29 of the endoscope 1. The space 24 defined by the interior of the optical inner shaft 22 is radially closer to the center of the outer shaft 2 than the space 23. The space 24 serves as both a flushing channel and as a channel for axially guiding the shaft of the auxiliary instrument.

As shown in FIG. 1, this eyepiece 29 is arranged at an angle to the main axis A of the endoscope 1. The optical inner shaft 22 terminates proximally in a closable connection part 33 and can be connected to a flushing source (not shown) via a connector 31, which can also be closed and which is arranged at an angle to the connection 33. The free space of the optical inner shaft 22 therefore serves, in this case, as both a flushing channel and as an auxiliary instrument guide channel.

In the embodiment shown, a laser probe 30 which has, on the proximal end, a coupling 35 for connection to a laser source (not shown) is shown as the auxiliary instrument. The laser probe consists of a probe shaft 32 having a relatively small diameter and of a probe head 34 on the distal end having a relatively large diameter. As can be noted from FIGS. 2 and 3, even when the laser probe 30 is introduced into the optical inner shaft 22 sufficient space remains for the flushing. Due to the oval shape of the optical outer shaft 21 of the optical system 20 when the latter is introduced into the endoscope outer shaft 2, spaces 35 (FIG. 2) are produced which are in communication with the suction connection 4. These spaces 38 are used as suction channels and the suction action is optimized by the aforementioned holes 6 in the distal end region of the endoscope outer shaft 2.

The measures proposed in accordance with the invention are also directed at modifying the endoscope for the use of the auxiliary instrument, for instance, in the form of a laser probe having a thick distal probe head 34, which is introduced by the so-called "backloading" process into the endoscope outer shaft 2, the probe head 34 being adapted to be deflected laterally and completely out of the field of view of the optical system 20. For this purpose, the outer shaft 2 has a groove-shaped recess 16 in its distal end section 5, and the optical system 20, i.e., the optical inner shaft 22 and the optical outer shaft 21, has a groove-shaped recess 36 in its distal end section 7. As shown in FIG. 3, the probe head 34 of the laser probe 30 is guided, upon the pulling back of the probe shaft 32 into the endoscope 1 by the edge of the recess 16 of the endoscope outer shaft 2, deflected downward and guided almost completely into the free space created as a whole by the recesses 16 and 36. The probe head 34 is thus brought completely out of the field of view F of the optical system 20.

Since in the embodiment shown, the optical axis B of the field of view F of the objective 26 of the optical system 20 assumes an angle with respect to the longitudinal axis A of the endoscope 1, so that the field of view F is directed forward and downward from the distal end of the endoscope 1, as shown in FIG. 3, it is important that the probe head 34 of the laser probe 30 can be withdrawn by pulling back the probe shaft 32 far into the recess 16 of the endoscope outer shaft 2 so that the field of view F is completely freed and is not impeded by the probe head 34. The probe head 34 in its fully inserted condition is pressed somewhat downward by the groove shape of the recesses 16 and 36, so that its longitudinal axis forms an angle with the axis A of the endoscope outer shaft 2. The edges 17 and 37 of the groove-shaped recesses 16 and 36 in the endoscope outer shaft 2 and in the optical shafts 21, 22 are rounded on all sides in order to make the endoscope non-traumatic.

So that the probe head 34 will be pressed downward upon the proximal pulling-back of the probe shaft 32 of the laser probe 30, and so that the probe head 34 can move in said angle of the field of view F, the width of the recess 16 of the endoscope outer shaft 2 and of the recess 36 of the optical system 20 must be greater than the diameter of the probe shaft 32 and of the probe head 34.

What is claimed is:

1. An endoscope (1), comprising: an endoscope outer shaft (2) and an optical system (20) each having a distal end; the endoscope further comprising a channel for an auxiliary instrument (30), the auxiliary instrument (30) having a shaft (32) and a distal probe head (34) which can be deflected into and out of the field of view (F) of the optical system (20) by axial movement of the auxiliary instrument (30); the distal ends of the endoscope outer shaft (2) and of the optical system (20) each having a groove-shaped recess (16, 36) defined by respective edges (17, 37), the edges of the recesses being configured such that upon the movement of the auxiliary instrument (30) into the endoscope (1), the distal probe head (34), guided by the edge (17) of the recess (16) of the endoscope outer shaft (2), is moved at least in part into the free space created by the recesses (16, 36) and, with lateral deflection, out of the field of view (F) of the optical system (20).

2. The endoscope according to claim 1, wherein the auxiliary instrument (30) is guided within the endoscope (1), and wherein the probe head (34) of the auxiliary instrument (30) has a length and a diameter, and wherein the shaft (32) of the auxiliary instrument (30) has a diameter, the diameter of the probe head (34) being greater than the diameter of the shaft (32).

3. The endoscope according to claim 1, wherein the recesses (16, 36) have a width greater than the diameter of the shaft (32) and an axial length approximately equal to the length of the probe head (34) of the auxiliary instrument (30).

4. The endoscope according to claim 1, wherein the optical system (20) further comprises an objective (26) and a plurality of optical fibers (27), the objective (26) being arranged on the distal end of the endoscope (1) such that the optical axis (B) of the field of view (F) is at an angle to the main axis (A) of the endoscope (1).

5. The endoscope according to claim 4, wherein the optical system (20) lies within the endoscope outer shaft (2) and has an optical outer shaft (21) and an optical inner shaft (22) within the optical outer shaft (21), the optical inner shaft (22) having a smaller height than the optical outer shaft (21), thereby creating two spaces (23, 24) in the optical system (20), the space (23) of the optical outer shaft (21)

containing the objective (26) and the optical fibers (27) and the space (24) of the inner shaft (22) serving as a flushing channel and as a channel for the axial guiding of the shaft (32) of the auxiliary instrument (30).

6. The endoscope of claim 5, wherein the endoscope outer shaft (2) is cylindrical, the optical outer shaft (21) is substantially oval and the optical inner shaft (22) is approximately oval.

7. The endoscope according to claim 5, wherein the space (24) of the optical inner shaft (22) which receives the shaft (32) of the auxiliary instrument (30) has a diameter which is greater than the diameter of the auxiliary instrument shaft (32).

8. The endoscope according to claim 6 wherein the outer shaft (2) further comprises an inner wall and the optical oval outer shaft (21) further comprises an outer wall, so that when the optical system (20) is introduced into the endoscope outer shaft (2), spaces (35) are produced between the inner wall of the cylindrical outer shaft (2) and the outer wall of the optical oval outer shaft (21) which serve as axial suction channels.

* * * * *